(12) United States Patent
Gagliardi et al.

(10) Patent No.: US 8,969,380 B2
(45) Date of Patent: Mar. 3, 2015

(54) SECONDARY 8-HYDROXYQUINOLINE-7-CARBOXAMIDE DERIVATIVES FOR USE AS ANTIFUNGAL AGENTS

(75) Inventors: Stefania Gagliardi, Vimercate (IT);
Simone Del Sordo, Treviglio (IT);
Federico Mailland, Lugano (CH);
Michela Legora, Appiano Gentile (IT)

(73) Assignee: Polichem SA, Luxembourg (LU)

( * ) Notice: Subject to any disclaimer, the term of this patent is extended or adjusted under 35 U.S.C. 154(b) by 148 days.

(21) Appl. No.: 13/519,439

(22) PCT Filed: Dec. 28, 2010

(86) PCT No.: PCT/EP2010/070791
§ 371 (c)(1),
(2), (4) Date: Aug. 27, 2012

(87) PCT Pub. No.: WO2011/080265
PCT Pub. Date: Jul. 7, 2011

(65) Prior Publication Data
US 2012/0329797 A1 Dec. 27, 2012

(30) Foreign Application Priority Data
Dec. 29, 2009 (EP) ..................................... 09180899

(51) Int. Cl.
| | | |
|---|---|---|
| *C07D 417/12* | (2006.01) |
| *C07D 401/12* | (2006.01) |
| *C07D 405/12* | (2006.01) |
| *C07D 413/12* | (2006.01) |
| *C07D 409/12* | (2006.01) |
| *C07D 215/48* | (2006.01) |

(52) U.S. Cl.
CPC ............ *C07D 401/12* (2013.01); *C07D 417/12* (2013.01); *C07D 405/12* (2013.01); *C07D 413/12* (2013.01); *C07D 409/12* (2013.01); *C07D 215/48* (2013.01)
USPC .......................................... 514/312; 514/311

(58) Field of Classification Search
USPC .................................. 514/311, 312
See application file for complete search history.

(56) References Cited

U.S. PATENT DOCUMENTS 6,500,842 B1 12/2002 Vaillancourt et al.
2003/0055071 A1 3/2003 Anthony et al.

FOREIGN PATENT DOCUMENTS

| EP | 1375486 | 1/2004 |
| EP | 1669348 | 6/2008 |
| WO | WO98/11073 | 3/1998 |
| WO | WO2008/014602 | 2/2008 |

OTHER PUBLICATIONS

International Search Report With Written Opinion for PCT/EP2010/070791 of Feb. 17, 2011.
IPRP for PCT/EP2010/070791 of Mar. 8, 2012.
Li, X., et al., Bioorganic and Medicinal Chemistry, vol. 14, No. 16, p. 5742-5755, Aug. 15, 2006.
Musiol, R., et al., Bioorganic and Medicinal Chemistry, vol. 16, No. 8, p. 4490-4499.
Polanski, J., et al., Letters in Drug Design and Discovery, vol. 4, No. 2, p. 99-105.
Warshakoon, et al., Biooranic and Medicinal Chemistry Letters, vol. 16, No. 21, p. 5517-5522, Nov. 1, 2006.
Bastert J. et al, Int. J. Antimicrob. Agents, 2001; 17, 81-91.
Cornely O. A. et al, Clin. Infect. Disc., 2007; 44, 1289-1297.
Dictar M. O. et al, Med Mycol., 2000; 38 Suppl. 1, 251-256.
Dumaine R., Roy M. L., Brown A. M., J. Pharmacol. Exp. Ther., 1998; 286, 727-735.
Hamacher J. et al, Eur. Respir. J., 1999; 13, 180-186.
Johnson L.B., Kauffman C. A., Clin. Infect. Dis., 2003, 36, 630-637.
Khan S. A., Wingard J. R., Natl. Cancer Inst. Monogr. 2001; 29, 31-36.
Korting H. C. et al, Antimicrob. Agents Chemother., 1993; 37, 2064-2068.
Magro C. M. et al, J. Cutan. Pathol., 2008; 35, 74-81.
Perveze Z. et al, Liver Transpl., 2007; 13. 162-164.
Sarosi G. A., Davies S. F., West J. Med., 1996; 164, 335-340.
Schelenz S., J. Antimicrob. Chemother. 2008; 61, Suppl 1, 31-34.
Sidoroff A. et al, Br. J. Dermatol., 2007; 15, 989-996.
Trot R. J. et al, Intensive Care Med., 2007; 33, 1694-1703.

*Primary Examiner* — Yong Chong
(74) *Attorney, Agent, or Firm* — Hueschen and Sage

(57) ABSTRACT

The present invention provides secondary 8-hydroxyquinoline-7-carboxamide derivatives of general formula (I) and pharmaceutically acceptable salts thereof. These compounds are useful as antifungal agents. Specifically, these compounds were tested against *Tricophyton Rubrum*, *Tricophyton Mentagrophytes*, *Aspergillus Niger* and *Scopulariopsis Brevicaulis*. These compounds are active against *Candida* species such as *Candida Albicans* and *Candida Glabrata*.

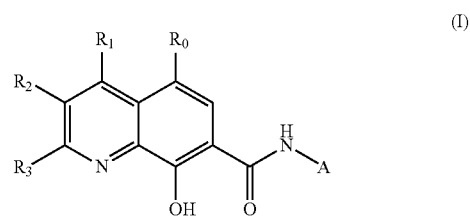

20 Claims, 3 Drawing Sheets

SECONDARY 8-HYDROXYQUINOLINE-7-CARBOXAMIDE DERIVATIVES FOR USE AS ANTIFUNGAL AGENTS

The present invention provides secondary 8-hydroxyquinoline-7-carboxamide derivatives and pharmaceutically acceptable salts thereof, for use as antifungal agents. Specifically, these compounds were tested against *Tricophyton Rubrum*, *Tricophyton Mentagrophytes*, *Aspergillus Niger* and *Scopulariopsis Brevicaulis*. These compounds are active against *Candida* species such as *Candida Albicans* and *Candida Glabrata*.

BACKGROUND OF THE INVENTION

Pathogenic fungi can be divided in two categories: fungi that are able to induce diseases in normal subjects and less invasive fungi that are able to produce diseases only in critically ill hosts. In the past two decades there was a significant increase in the incidence of invasive opportunistic fungal infections and associated morbidity and mortality. This is mainly due to the major advances in modern medicine that have increased the survival of critical patients such as those in intensive care units (ICU) with intravascular and urinary catheters, total parenteral nutrition and hemodialysis or connected to ventilatory systems.

*Candida* species commonly cause nosocomial blood stream infections among patients in the ICU. The UK hospitalized incidence of candidemia is about 3 per 100,000 bed days, and 40% to 52% of all cases occur in ICU (Schelenz S., *J. Antimicrob. Chemother.* 2008; 61, Suppl 1, 31-34). This kind of mycoses is frequently associated with considerable morbidity and mortality.

The attributable mortality rate is about 38%, although it can vary between 5% and 71%. During recent years there was a rising incidence of invasive pulmonary aspergillosis in patients admitted to ICU. The disease incidence ranges from 0.3% to 5.8% with an overall mortality rate exceeding 80% (Trof R. J. et al, *Intensive Care Med.*, 2007; 33, 1694-1703). Critically ill patients are at risk to develop disturbances in immunoregulation during their stay in the ICU, which render them more vulnerable to fungal infections. Risk factors such as chronic obstructive pulmonary disease, prolonged use of steroids, advanced liver disease, chronic renal replacement therapy, near-drowning and diabetes mellitus have been described.

There was a dramatic increase also in the number of immunocompromised patients especially in the fields of solid organ and bone marrow transplantation, autoimmune syndromes, acquired immune deficiency syndrome (AIDS) and oncology.

About 40% of bone marrow transplant population develops invasive fungal infection (Khan S. A., Wingard J. R., Natl. Cancer Inst. Monogr. 2001; 29, 31-36). *Candida* and *Aspergillus* species are the most common pathogens responsible for nosocomial superficial and invasive mycoses in hematologic malignancies and bone marrow transplanted patients. In these patients the mortality associated with the systemic candidosis is very high (50-90%). Regarding solid organs transplantation, infective complications are more frequent in lung-transplanted patients. In addition to the immunosuppressive regimen, the increased susceptibility is mainly due to the constant exposure to the external environment. Parallel to immunosuppressive treatment intensity, invasive fungal infection may occur during the first days after surgical operation, its frequency is highest in the first two months and decreases after 6 months but it can occur also years after transplantation (Hamacher J. et al, *Eur. Respir. J.*, 1999; 13, 180-186).

Invasive fungal infections are also frequent in other kind of solid organ transplantation such as kidney and liver transplants for which incidence of 5 to 50% are reported (Dictar M. O. et al, *Med Mycol.*, 2000; 38 Suppl. 1, 251-258).

Mycoses are one of the major causes of morbidity in patients with AIDS and the incidence and severity of these infections increase with disease progression and the consequent impairment of T-cell-mediated immunity. The incidence of the different mycoses is closely related to the endemic opportunistic fungi present in the area of residence. Generally speaking the most frequent mycoses that affect AIDS patients are histoplasmosis, blastomycosis, coccidioidomycosis and paracoccidiomycosis (Sarosi G. A., Davies S. F., *West J. Med.*, 1996; 164, 335-340).

Mucosal *Candida* infections are also extremely common. In normal patients all these mycosis are usually self-limited but in immunodepressed patients become highly invasive resulting in progressive and widespread dissemination.

Moreover, the increase of mycosis caused by organism resistant to current therapies became evident over recent years. This phenomenon is particularly evident for fungal infections caused by *Candida albicans* and fluconazole and other azoles (Bastert J. et al, *Int. J. Antimicrob. Agents*, 2001; 17, 81-91).

The antimycotic drugs currently available are not fully satisfactory due to their limited activity spectrum and to the heavy side effects associated to their use. The polyene drug Amphotericin B, for example, is active against *Aspergillus*, Zygomycete and other molds anyway, and due to its toxicity the licensed dosage for treatment of invasive mycosis is 3-5 mg/kg per day. In highly immunocompromised patients with invasive aspergillosis, liposomal encapsulated Amphotericin B, daily administered at 3 mg/kg, gave a favorable response in 50% of patients and 12-week survival rate of 72% (Cornely O. A. et al, *Clin. Infect. Dis.*, 2007; 44, 1289-1297). The drug induced nephrotoxicity and hypokalemia in 14-16% of the patients. When daily administered at 10 mg/kg, Amphotericin B did not give any additional benefit and caused higher rates of nephrotoxicity (31%).

Azoles, introduced in the second half of the 1970s, are blockers of ergosterol synthesis. The use of the drugs belonging to this family is limited by their narrow spectrum of activity. Voriconazole, for example, is more active than Amphotericin B for the treatment of invasive aspergillosis but has no activity against zygomycetes (Johnson L. B., Kauffman C. A., *Clin. Infect. Dis.*, 2003, 36, 630-637). The azoles employment is also limited by the induction of several side effects. Azoles interact with mammalian p450 enzymes resulting in interference with the metabolism of other drugs and, in addition, some azoles such as ketoconazole are able to block the cardiac potassium channel Kv1.5 causing Q-T prolongation and 'torsade de pointes' (Dumaine R., Roy M. L., Brown A. M., *J. Pharmacol. Exp. Ther.*, 1998; 286, 727-735).

Allylamines such as Terbinafine bind to and inhibit squalene epoxidase resulting in a block of ergosterol synthesis. These drugs are very potent against Dermatophytes while their activity against *Candida* species is very poor. In some cases treatment with allylamines is followed by severe cutaneous adverse reactions. A recent multinational case-control study (euroSCAR) (Sidoroff A. et al, *Br. J. Dermatol.*, 2007; 15, 989-996) revealed that Terbinafine systemic treatment is strongly associated with the development of an acute generalized exanthematous pustolosis (AGEP). This disease is characterized by the rapid occurrence of many sterile, nonfollicular pustules, usually accompanied by leucocytosis and fever. AGEP is generally attributed to the patient treatment with particular drugs and seems to be related to an altered T cells activity. Terbinafine treatment might also induce dermatomyositis, a severe autoimmune connective tissue disease characterized by erythema, muscle weakness and interstitial pulmonary fibrosis (Magro C. M. et al, *J. Cutan. Pathol.*, 2008; 35, 74-81). In addition, as a variety of antifungal medications, Terbinafine might cause severe liver injuries (Perveze Z. et al, *Liver Transpl.*, 2007; 13, 162-164).

Griseofulvin is a benzofurane introduced in 1960 for the treatment of dermatophyte infections. The compound induces its fungistatic activity by interfering with microtubule production. Griseofulvin displays limited activity in the treatment of onychomycoses and frequently causes severe side effects such as nausea, diarrhea, headache, confusion and fatigue (Korting H. C. et al, *Antimicrob. Agents Chemother.*, 1993; 37, 2064-2068) that can cause the treatment discontinuation.

The two N-Hydroxy pyridones, Ciclopirox olamine and Octopirox, seem to mainly act by chelating polyvalent cations, resulting in the inhibition of the metal-dependent enzymes. They are employed against different fungal infections but their use is limited to topical treatment.

The echinocandins (Caspofungin, Micafungin, Anidulafungin) are semi-synthetic lipo-peptides and are the most recently introduced antimycotic drugs. They act by non-competitively inhibiting β-(1-3)-Dglucan synthase, an enzyme essential for the maintenance of the cell wall and are mainly used for intravenous treatment of invasive candidiasis and aspergillosis. They are fungicidal against yeast but only fungistatic against filamentous fungi; in addition, they are quite inactive against dimorphic fungi such as *Blastomyces* and *Histoplasma*. Echinocandins are generally well tolerated but animal reproduction studies showed adverse effects on fetus. For this reason FDA lists echinocandins as a pregnancy-risk category (http://www.fda.gov/medwatch/SAFETY/2004/mar_PI/Cancidas_PI.pdf; http://www-.fda.gov/medwatch/safety/2007/Aug_PI/Mycamine_PI.pdf). WO98/11073 (U.S. Pat. No. 6,310,211) discloses 8-hydroxy-7-substituted quinolines as anti-viral agents.

US2003/0055071 discloses a generic class of compounds having HIV integrase inhibitory activity. As a matter of fact, most of the specific compounds disclosed in this reference bear a naphthydrinyl residue.

EP1375486 discloses nitrogen-containing heteroaryl compounds having HIV integrase inhibitory activity. N-benzyl-8-hydroxyquinoline-7-carboxamide. WO2008/14602 discloses quinoline derivatives active as CLK-1 inhibitors. EP1669348 discloses antifungal agents defined by a very broad formula which includes certain secondary amides.

From what described above, it is evident that the clinical need for efficacious antifungal drugs has dramatically increased in the few last years. Unfortunately the drugs actually available are not satisfactory due to their narrow spectrum of action, pharmacokinetic properties and severe side effects.

DESCRIPTION OF THE INVENTION

The present invention particularly provides compounds of general formula (I), endowed with a potent antifungal activity

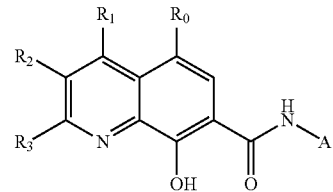

wherein $R_0$ is:
—H,
—F,
—Cl,
—Br,
—$NO_2$,
—$CF_3$,
—$CO_2R_{11}$,
—(C=O)—$NR_{14}R_{15}$,
—$C_1$-$C_6$ alkyl,
—CN,
—$(CH_2)_m$—$NR_{14}R_{15}$,
—$(SO_2)$—$NR_{14}R_{15}$,
—(N—C=O)—$NR_{14}R_{15}$,
—W—$R_{10}$,
—$(CH_2)_m$-aryl, optionally substituted by one, two or three $R_4$, or
—$(CH_2)_m$-heterocycle, optionally substituted by one or two $R_5$;
wherein $R_1$ is:
—H,
—$C_1$-$C_3$ alkyl,
—OH, or
—$CF_3$;
wherein $R_2$ is:
—H, or
—$CH_2$-phenyl, optionally substituted by one $R_6$;
wherein $R_3$ is:
—H,
—$C_1$-$C_3$ alkyl,
—OH,
—$CF_3$,
—CH=CH-furanyl,
—CH=CH-phenyl, optionally substituted by one $R_4$,
—CH=CH-pyridinyl,
—$(CH_2)_m$-phenyl optionally substituted by one $R_4$,
—NHV,
—$CH_2$NHV, or
—$CH_2$Z;
wherein $R_4$ is:
—F,
—Cl,
—Br,
—I,
—$NO_2$,
—$CF_3$,
—CN,
—$CH_2OH$
—$C_1$-$C_6$ alkyl,
—W—$R_{10}$
—$(CH_2)_m$-aryl, optionally substituted by one or two $R_5$,
—$(CH_2)_m$-heterocycle, optionally substituted by one or two $R_5$,
—$(CH_2)_m$—$C_3$-$C_8$ cycloalkyl, optionally substituted by one $R_8$,
—$SO_2$—NH-heterocycle, —$(CH_2)_m$—$NR_{14}R_{15}$,
—$(SO_2)$—$NR_{14}R_{15}$,
—$(C\!=\!O)$—$NR_{14}R_{15}$, or
—$(N\!-\!C\!=\!O)$—$NR_{14}R_{15}$;
wherein $R_5$ is:
—H,
—F,
—Cl,
—Br,
—$CF_3$,
—W—$R_{10}$,
—$C_1$-$C_6$ alkyl,
—$(CH_2)_m$-aryl, optionally substituted by one or two $R_6$,
—$(CH_2)_m$-heterocycle, optionally substituted by one or two $R_7$, or
—$(CH_2)_m$—$C_3$-$C_8$ cycloalkyl;
wherein $R_6$ is:
—F,
—Cl, or
—Br;
wherein $R_7$ is:
—H,
—F,
—Cl,
—Br,
—OH, or
—O—$C_1$-$C_3$ alkyl;
wherein $R_8$ is:
—$C_1$-$C_4$ alkyl,
—W—H,
—$CH_2$—W—H,
—$(CH_2)_m$-aryl, optionally substituted by one or two $R_6$, or
—$(CH_2)_m$-heterocycle, optionally substituted by one or two $R_7$;
wherein $R_9$ is:
—$C_1$-$C_7$ alkyl,
—$C_3$-$C_8$ cycloalkyl,
—$C(O)R_{11}$,
—$C(O)NHR_{11}$,
—$C(OH)R_{11}$,
—$CH_2OH$,
—$CO_2R_{11}$, or
-aryl optionally substituted by one or two $R_4$;
wherein $R_{10}$ is:
—H,
—$C_1$-$C_6$ alkyl,
—$(CH_2)_m$-aryl, optionally substituted by one or two $R_4$,
—$(CH_2)_m$-heterocycle, optionally substituted by one or two $R_5$,
—$(CH_2)_m$—$C_3$-$C_8$ cycloalkyl, or
—$CH(R_{12})R_{13}$;
wherein $R_{11}$ is:
—H,
—$C_1$-$C_7$ alkyl,
—$(CH_2)_mX_1$, or
—$(CH_2)_m$—$C_3$-$C_8$ cycloalkyl;
wherein $R_{12}$ is:
—H,
—$(CH_2)_mCO_2$—$C_1$-$C_6$ alkyl,
—$(CH_2)_m$-phenyl, optionally substituted by one or two $R_7$,
—$(CH_2)_m$-heterocycle, optionally substituted by one or two $R_5$,
—$C_1$-$C_6$ alkyl, optionally substituted by one $R_6$,
—$C_1$-$C_4$ alkyl NH—$COOCH_2$-benzyl, or
—$C_1$-$C_4$ alkyl-S—$CH_3$;
wherein $R_{13}$ is:
—NH—$CO_2C(CH_3)_3$,
—CN,
—COOH, or
—$CO_2R_{11}$;
wherein $R_{14}$ and $R_{15}$, independently from each other, are selected from:
—H,
—$C_1$-$C_6$ alkyl,
—$(CH_2)_m$-aryl, optionally substituted by one, two or three $R_4$,
—$(CH_2)_m$-cycloalkyl, optionally substituted by one $R_8$,
—$(CH_2)_m$-heterocycle optionally substituted by one or two $R_5$,
—$(CH_2)_m$—W—$R_{10}$,
—$(CH_2)_m$—CN,
taken together with the nitrogen atom to which they are bound to form an optionally substituted 5- to 8-membered heteromonocycle containing from one to three heteroatoms selected from the group consisting of nitrogen, oxygen and sulphur, or
taken together with the nitrogen atom to which they are bound to form an optionally substituted 5- to 8-membered heteromonocycle which is fused to one or two optionally substituted saturated or unsaturated rings or to other optionally substituted heterocycles containing from one to three heteroatoms selected from the group consisting of nitrogen, oxygen and sulphur;
wherein A is:
—$(CH_2)_m$—$X_1$,
—$(CH_2)_m$—$C_3$-$C_8$ cycloalkyl, optionally substituted by one $R_8$,
—$(CH_2)_m$—W—$X_2$,
—$(CH_2)_m$—W—$CH_2$—$X_1$, or
—$(CH_2)_m$—$CHR_9$—$(CH_2)_m$—$X_1$;
wherein $X_1$ is:
-aryl, optionally substituted by one, two or three $R_4$,
-heterocycle, optionally substituted by one or two $R_5$,
—$C_1$-$C_8$ alkyl,
—CH(OH)-phenyl,
—S-phenyl,
—$NHSO_2$-phenyl, optionally substituted by one, two or three $R_4$,
—CN,
—OH,
—$C_3$-$C_8$ cycloalkyl, optionally substituted by one or two $R_8$, or
-4-cyano-2,3,4,5-tetrafluoro-phenyl;
wherein $X_2$ is:
-aryl, optionally substituted by one, two or three $R_4$,
-heterocycle, optionally substituted by one or two $R_5$,
—$C_1$-$C_8$ alkyl,
—CH(OH)-phenyl, or
—$C_3$-$C_8$ cycloalkyl, optionally substituted by one or two $R_8$;
wherein W is:
—NH—,
—O—, or
—S—;
wherein V is:
—$R_{11}$,
—$C(O)R_{11}$,
—$SO_2R_{11}$, or
—$C(O)NHR_{11}$;
wherein Z is:
—$C_1$-$C_7$ alkyl,
—$C_3$-$C_8$ cycloalkyl,
—$C(O)R_{11}$,
—$C(O)NHR_{11}$, or —CO$_2$R$_{11}$;
wherein aryl is:
phenyl,
naphtyl,
biphenyl,
tetrahydro-naphthyl, or
fluorenyl;
wherein heterocycle is a 5-, 6- or 7-membered saturated or unsaturated ring containing from one to three heteroatoms selected from the group consisting of nitrogen, oxygen and sulphur, and including any bicyclic group in which any of the above heterocyclic rings is fused to a benzene ring or another heterocyclic;
wherein cycloalkyl is a saturated or unsaturated hydrocarbon ring including any bicyclic group in which the above ring is connected to a benzene, heterocyclic or other hydrocarbon ring;
wherein m is an integer from 0 to 6;
or a pharmaceutically acceptable salt or derivative thereof.
Further preferably in formula I:
R$_0$, R$_1$, R$_2$ and R$_3$ are H;
A is —(CH$_2$)$_m$—X$_1$;
m is an integer from 0 to 1;
X$_1$ is
-aryl, optionally substituted by one or two R$_4$,
-heterocycle, optionally substituted by one or two R$_5$, or
—C$_3$-C$_8$ cycloalkyl optionally substituted by one or two R$_8$;
wherein R$_5$ and R$_8$ are as defined above;
R$_4$ is
—Cl,
—Br,
—CF$_3$,
—W—R$_{10}$, or
—(CH$_2$)$_m$—NR$_{14}$R$_{15}$;
W is oxygen;
R$_{10}$ is
—H, or
—C$_1$-C$_6$ alkyl;
R$_{14}$ and R$_{15}$, are
—C$_1$-C$_6$ alkyl, or
taken together with the nitrogen atom to which they are bound to form an optionally substituted 5- to 8-membered heteromonocycle containing from one to three heteroatoms selected from the group consisting of nitrogen, oxygen and sulphur;
aryl is preferably phenyl;
and/or heterocycle is preferably 2,3-dihydrobenzo[b][1,4]dioxine, pyridine, thiophene, triazole, thiazole, isoxazole, benzothiazole, pyrazine, imidazole or furane.

"Pharmaceutically acceptable salts or derivatives" refers to those salts or derivatives which possess the biological effectiveness and properties of the parent compound and which are not biologically or otherwise undesirable. Such salts include those with inorganic or organic acids, as for instance, the hydrobromide, hydrochloride, sulfate, phosphate, sodium salt, magnesium salt; such derivatives include the esters, the ethers and the N-oxides.

The compounds of the present invention and their pharmaceutical acceptable salts or derivatives may have asymmetric centres and may occur, except when specifically noted, as mixtures of stereoisomers or as individual diastereomers, or enantiomers, with all isomeric forms being included in the present invention.

The phrase "pharmaceutically acceptable", as used in connection with the formulations containing the compounds of the invention, refers to molecular entities and other ingredients of such formulations that are physiologically tolerable and do not typically produce untoward reactions when administered to an animal such as a mammal (e.g., a human). Preferably, as used herein, the term "pharmaceutically acceptable" means approved by a regulatory agency, such as the FDA or the EMEA, or listed in the U.S. or European Pharmacopeia or other generally recognized pharmacopeia for use in mammals, and more particularly in humans.

Preferred compounds of the invention include but are not limited to compounds selected from the group consisting of:
8-Hydroxy-N-(thiophen-2-ylmethyl)quinoline-7-carboxamide
8-Hydroxy-N-(cyclohexylmethyl)quinoline-7-carboxamide
8-Hydroxy-N-benzyl-quinoline-7-carboxamide
8-Hydroxy-N-(4-chlorobenzyl)quinoline-7-carboxamide
8-Hydroxy-N-(4-methoxyphenyl)quinoline-7-carboxamide
8-Hydroxy-N-(4-(trifluoromethyl)benzyl)quinoline-7-carboxamide
8-Hydroxy-N-phenyl-quinoline-7-carboxamide
8-Hydroxy-N-(2-hydroxybenzyl)quinoline-7-carboxamide
8-Hydroxy-N-(furan-2-ylmethyl)quinoline-7-carboxamide
8-Hydroxy-N-(pyridin-3-ylmethyl)quinoline-7-carboxamide
8-Hydroxy-N-(4-methoxybenzyl)quinoline-7-carboxamide
8-Hydroxy-N-(4-bromobenzyl)quinoline-7-carboxamide
8-Hydroxy-N-(1,1-dioxidotetrahydrothien-3-yl)quinoline-7-carboxamide
8-Hydroxy-N-(4-(dimethylamino)benzyl)quinoline-7-carboxamide
8-Hydroxy-N-(tetrahydro-2H-pyran-4-yl)quinoline-7-carboxamide
8-Hydroxy-N-(4-morpholinophenyl)quinoline-7-carboxamide
8-Hydroxy-N-(4-(1H-1,2,4-triazol-1-yl)phenyl)quinoline-7-carboxamide
8-Hydroxy-N-(thiazol-2-yl)quinoline-7-carboxamide
8-Hydroxy-N-(2,3-dihydrobenzo[b][1,4]dioxin-6-yl)quinoline-7-carboxamide
8-Hydroxy-N-(4-morpholinobenzyl)quinoline-7-carboxamide
8-Hydroxy-N-((5-methylisoxazol-3-yl)methyl)quinoline-7-carboxamide
8-Hydroxy-N-((4-methylthiazol-2-yl)methyl)quinoline-7-carboxamide
8-Hydroxy-N-(isoxazol-3-yl)quinoline-7-carboxamide
8-Hydroxy-N-(benzo[d]thiazol-2-ylmethyl)quinoline-7-carboxamide
8-Hydroxy-N-((5-methylpyrazin-2-yl)methyl)quinoline-7-carboxamide
8-Hydroxy-N-((1-methyl-1H-imidazol-2-yl)methyl)quinoline-7-carboxamide
8-Hydroxy-N-((4-phenylthiazol-2-yl)methyl)quinoline-7-carboxamide
8-Hydroxy-N-(pyridin-4-ylmethyl)quinoline-7-carboxamide
8-Hydroxy-N-(pyridin-2-ylmethyl)quinoline-7-carboxamide The compounds of the present invention can be prepared by the coupling of suitable 8-hydroxyquinolin-7-carboxylic acids 1-1 (or acid derivatives such as acid halides or esters) with the appropriate amines 1-2, as represented by the following general Chart 1:

CHART 1

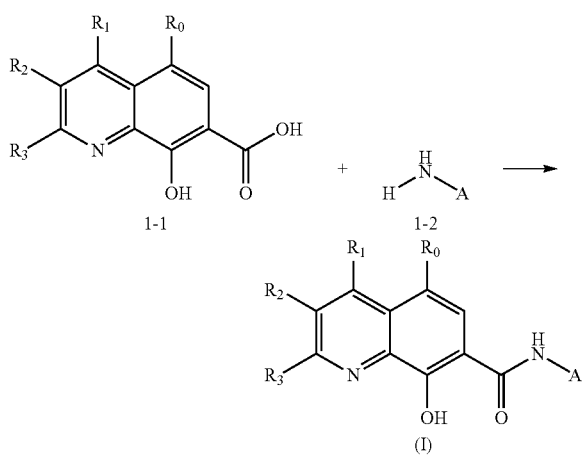

Alternatively the hydroxyl group of the carboxylic acid can be protected (as described in *Bioorg. Med. Chem.*, 14, 2006, 5742-5755 or *Synthesis*, 12, 1997, 1425-1428 or DE540842) before performing the coupling with the amine and deprotected in the final stage.

Methods for coupling carboxylic acids with amines to form carboxamides are well known in the art. Suitable methods are described, for example, in Jerry March, *Advanced Organic Chemistry*, 4th edition, John Wiley & Sons, 1992, pp. 417-425.

Methods for protecting and deprotecting aromatic hydroxyl groups are well known in the art. Protecting groups are manipulated according to standard methods of organic synthesis (Green T. W. and Wuts P. G. M. (1991) *Protecting Groups in Organic Synthesis*, John Wiley et Sons).

It will be apparent to those skilled in the art that the described synthetic procedures are merely representative in nature and that alternative synthetic processes are known to one of ordinary skill in organic chemistry.

Figure 1:
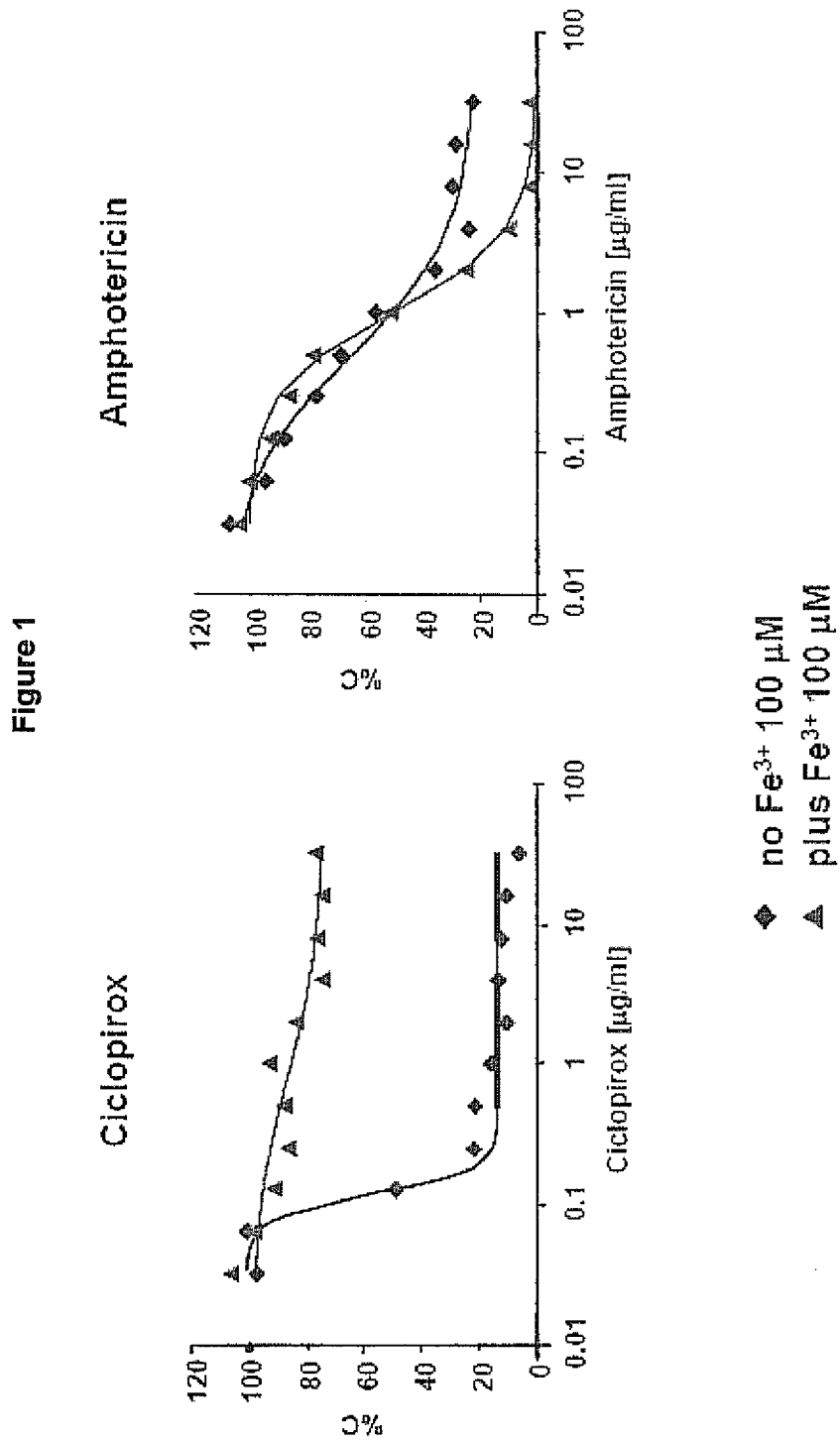
FIG. 1 shows the antifungal activity of ciclopirox and amphotericin in the presence and absence of $Fe^{3+}$.

The following examples serve only to illustrate the invention and its practice. The examples are not to be constructed as limitation on the scope or spirit of the invention.

EXPERIMENTAL SECTION

1. Chemical Synthesis

Unless otherwise indicated, all the starting reagents were found to be commercially available and were used without any prior purification. The compounds of the present invention can be readily prepared using conventional synthetic procedure. In these reactions, it is also possible to make use of variants which are themselves known to those of ordinary skill in this art, but are not mentioned in greater detail. Furthermore, other methods for preparing compounds of this invention will be readily apparent to the person of ordinary skill in the art in light of the following reaction schemes and examples. Unless otherwise indicated, all variables are as defined above. Where reference is made to the use of an "analogous" procedure, as will be appreciated by those skilled in the art, such a procedure may involve minor variation, for example reaction temperature, reagent/solvent amount, reaction time, work-up conditions or chromatographic purification conditions. Abbreviations used in the instant specification, particularly in the Tables and in the Examples, are summarized in Table 1.

TABLE 1

| | |
|---|---|
| LC-MS (Liquid Chromatography Mass Spectrum) | ESI (Electro Spray Ionization) |
| UPLC (Ultra Performance Liquid Chromatography) | $R_t$ (retention time in minutes) |
| | min (minutes) |
| | h (hours) |
| TFA (Trifluoroacetic acid) | RT (room temperature) |
| µm (micrometers) | $CH_3CN$ (Acetonitrile) |
| mmol (millimoles) | THF (Tetrahydrofuran) |
| µL (microlitres) | MeOH (Methanol) |
| DMSO (Dimethyl sulfoxide) | $Na_2SO_4$ (Sodium sulphate) |
| DCM (Dichloromethane) | |
| SPE-SI (Solid phase extraction with Silica gel) | |
| CFU (Colony Forming Unit) | |

Except where otherwise indicated, all temperatures are expressed in ° C. (degrees centigrade) or K (Kelvin).

Proton Nuclear Magnetic Resonance ($^1$H-NMR) spectra were recorded on a Brucker 300 MHz. Chemical shifts are expressed in parts of million (ppm, δ units). Splitting patterns describe apparent multiplicities and are designated as s (singlet), d (doublet), t (triplet), q (quartet), quint (quintet), sxt (sextet), m (multiplet), br. s (broad singlet).

LC-MS were recorded under the following conditions:

Method A-C HPLC with Sample Manager and 2996 PDA Detector (Waters) interfaced with a Mass Spectrometer Single Quadrupole ZQ (Waters). ZQ interface: ESI positive mode. Full scan from 102 to 900 amu. Capillary 3.2V, cone 25V, extractor 3V, RF 0.3V, source temperature 115° C., desolvation temperature 350° C., gas flow 800 Uh, cone 100 Uh.

Method A: Column Aquity HPLC-BEH C18 (50×2.1 mm, 1.7 µm). Flow rate 0.6 mL/min, column at 40° C., injection 2 µL. Mobile phases: A phase=water/$CH_3CN$ 95/5+0.1% TFA, B phase=water/$CH_3CN$=5/95+0.1% TFA. Gradient: 0-0.25 min (A: 95%, B: 5%), 3.30 min (A: 0%, B: 100%), 3.30-4.00 (A: 0%, B: 100%), 4.10 min (A: 95%, B: 5%), 4.10-5.00 min (A: 95%, B: 5%).

Method B: Column Atlantis dC18 (100×2.1 mm, 3.0 µm). Flow rate 0.3 mL/min, column at 40° C., injection 2 µL. Mobile phases: A phase=water/$CH_3CN$ 95/5+0.1% TFA, B phase=water/$CH_3CN$=5/95+0.1% TFA. Gradient: 0-0.20 min (A: 95%, B: 5%), 5.00 min (A: 0%, B: 100%), 5.00-6.00 (A: 0%, B: 100%), 6.10 min (A: 95%, B: 5%), 6.10-7.00 min (A: 95%, B: 5%).

Example 1

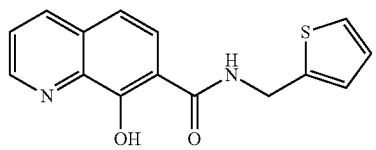 [SMILES: O=C(NCc1cccs1)c1ccc2cccnc2c1O]

8-Hydroxy-N-(thiophen-2-ylmethyl)quinoline-7-carboxamide

A mixture of 8-hydroxyquinoline-7-carboxylic acid (100 mg, 0.53 mmol) and di(1H-imidazol-1-yl)methanone (86 mg, 0.53 mmol) in THF (8 mL) was heated to 45° C. overnight, under nitrogen. The reaction mixture was allowed to cool to RT and thiophene-2-ylmethanamine (30 mg, 0.26 mmol) was added. The resulting mixture was stirred at RT for 24 h. Additional thiophene-2-ylmethanamine (15 mg, 0.1.3 mmol) was added and the reaction mixture was stirred for 60 h at RT. The reaction mixture was quenched with H$_2$O and THF was evaporated to dryness. Saturated solution of sodium hydrogen carbonate was added to the aqueous phase and extracted twice with DCM. The separated organics were dried over Na$_2$SO$_4$, filtered and concentrated under reduced pressure. The residue was purified by SPE-SI cartridge (2 g, DCM to DCM:MeOH 99:1) affording the title compound (40 mg, 0.14 mmol) as a yellow solid.

LC-MS m/z (ESI$^+$): 285.1 (MW), R$_t$=1.41 min (Method A).

$^1$H-NMR (DMSO-d$_6$) δ: 9.43 (br. s, 1H); 8.91 (dd, 1H); 8.35 (dd, 1H); 8.00 (d, 1H); 7.65 (dd, 1H); 7.31-7.48 (m, 2H); 7.09 (dd, 1H); 6.99 (dd, 1H); 4.40-4.92 (m, 2H)

Following the procedure described above, the additional compounds of the present invention were prepared (Table 2).

TABLE 2

| Ex. | Chemical name | $^1$H-NMR (DMSO-d$_6$) | LC-MS method | R$_t$; [MH$^+$] |
|---|---|---|---|---|
| 2 | <br>8-Hydroxy-N-(cyclohexylmethyl)quinoline-7-carboxamide | δ: 8.90 (dd, 1H); 8.86 (t, 1H); 8.34 (dd, 1H); 8.00 (d, 1H); 7.64 (dd, 1H); 7.41 (d, 1H); 3.14-3.31 (m, 2H); 1.38-1.96 (m, 6H); 0.72-1.36 (m, 5H) | A | 1.81; 285.2 |
| 3 | 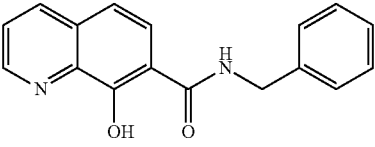<br>8-Hydroxy-N-benzyl-quinoline-7-carboxamide | δ: 9.33 (t, 1H); 8.92 (dd, 1H); 8.36 (dd, 1H); 8.03 (d, 1H); 7.65 (dd, 1H); 7.44 (d, 1H); 7.20-7.41 (m, 5H); 4.60 (d, 2H) | A | 1.50; 279.1 |
| 4 | 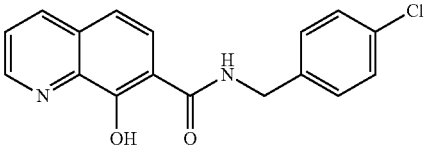<br>8-Hydroxy-N-(4-chlorobenzyl)quinoline-7-carboxamide | δ: 9.34 (t, 1H); 8.92 (dd, 1H); 8.36 (dd, 1H); 8.01 (d, 1H); 7.66 (dd, 1H); 7.44 (d, 1H); 7.41 (s, 4H); 4.42-4.73 (m, 2H) | A | 1.77; 313.1 |
| 5 | 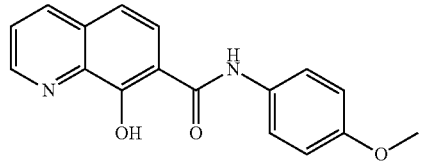<br>8-Hydroxy-N-(4-methoxyphenyl)quinoline-7-carboxamide | (353K) δ: 11.15 (br. s, 1H); 8.87 (d, 1H); 8.31 (dd, 1H); 8.06 (d, 1H); 7.62-7.68 (m, 2H); 7.60 (dd, 1H); 7.28 (d, 1H); 6.82-7.03 (m, 2H); 3.79 (s, 3H) | A | 1.51; 295.1 |
| 6 | 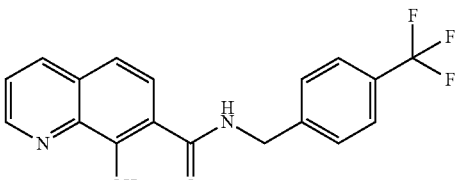<br>8-Hydroxy-N-(4-(trifluorobenzyl)benzyl)quinoline-7-carboxamide | δ: 9.46 (t, 1H); 8.92 (dd, 1H); 8.36 (dd, 1H); 8.01 (d, 1H); 7.72 (m, 2H); 7.66 (dd, 1H); 7.60 (m, 2H); 7.43 (d, 1H); 4.68 (d, 2H) | A | 1.90; 347.1 |

TABLE 2-continued

| Ex. | Chemical name | ¹H-NMR (DMSO-d₆) | LC-MS method | $R_t$; [MH⁺] |
|---|---|---|---|---|
| 7 | 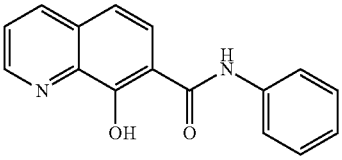<br>8-Hydroxy-N-phenyl-quinoline-7-carboxamide | δ: 11.06 (br. s, 1H); 8.93 (d, 1H); 8.47 (d, 1H); 8.06 (d, 1H); 7.63-7.88 (m, 3H); 7.28-7.53 (m, 3H); 6.99-7.19 (m, 1H) | A | 1.43; 265.1 |
| 8 | 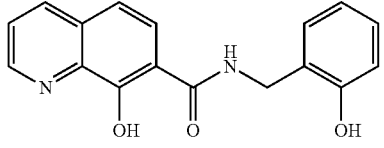<br>8-Hydroxy-N-(2-hydroxybenzyl)quinoline-7-carboxamide | δ: 9.63 (br. s, 1H); 9.19 (t, 1H); 8.92 (dd, 1H); 8.36 (dd, 1H); 8.06 (d, 1H); 7.66 (dd, 1H); 7.43 (d, 1H); 7.21 (dd, 1H); 6.99-7.16 (m, 1H); 6.84 (dd, 1H); 6.77 (td, 1H); 4.54 (d, 2H) | A | 1.26; 295.1 |
| 9 | <br>8-Hydroxy-N-(furan-2-ylmethyl)quinoline-7-carboxamide | δ: 9.27 (t, 1H) 8.91 (dd, 1H) 8.35 (dd, 1H) 8.01 (d, 1H) 7.65 (dd, 1H) 7.61 (dd, 1H) 7.41 (d, 1H) 6.42 (dd, 1H) 6.30-6.39 (m, 1H) 4.59 (d, 2H) | A | 1.23; 269.2 |
| 10 | 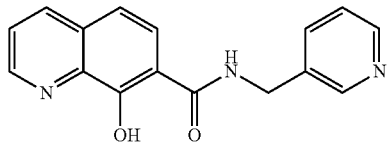<br>8-Hydroxy-N-(pyridin-3-ylmethyl)quinoline-7-carboxamide | δ: 9.44 (t, 1H); 8.91 (dd, 1H); 8.61 (d, 1H); 8.48 (dd, 1H); 8.35 (dd, 1H); 7.99 (d, 1H); 7.75-7.82 (m, 1H); 7.65 (dd, 1H); 7.41 (d, 1H); 7.38 (ddd, 1H); 4.62 (d, 2H) | B | 2.08; 280.14 |
| 11 | 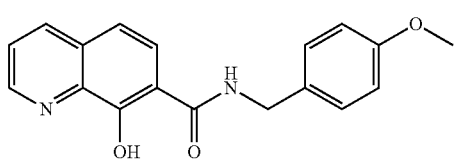<br>8-Hydroxy-N-(4-methoxybenzyl)quinoline-7-carboxamide | δ: 9.24 (t, 1H); 8.91 (dd, 1H); 8.35 (dd, 1H); 8.02 (d, 1H); 7.65 (dd, 1H); 7.42 (d, 1H); 7.32 (m, 2H); 6.91 (m, 2H); 4.34-4.66 (m, 2H); 3.74 (s, 3H). | A | 1.47; 309.1 |
| 12 | 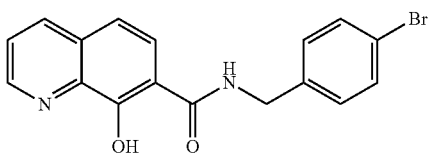<br>8-Hydroxy-N-(4-bromobenzyl)quinoline-7-carboxamide | δ: 9.35 (t, 1H); 8.92 (dd, 1H); 8.36 (dd, 1H); 8.00 (d, 1H); 7.66 (dd, 1H); 7.49-7.60 (m, 2H); 7.44 (d, 1H); 7.29-7.40 (m, 2H); 4.43-4.70 (m, 2H). | A | 1.74; 357.0 |
| 13 | 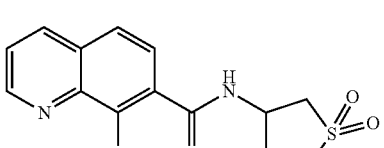<br>8-Hydroxy-N-(1,1-dioxidotetrahydrothien-3-yl)quinoline-7-carboxamide | δ: 9.09 (d, 1H); 8.92 (dd, 1H); 8.37 (dd, 1H); 7.97 (d, 1H); 7.66 (dd, 1H); 7.43 (d, 1H); 4.58-4.93 (m, 1H); 3.56 (dd, 1H); 3.37 (ddd, 1H); 3.09-3.30 (m, 2H); 2.55-2.61 (m, 1H); 2.14-2.40 (m, 1H). | A | 0.77; 307.1 |

TABLE 2-continued

| Ex. | Chemical name | ¹H-NMR (DMSO-d₆) | LC-MS method | R$_t$; [MH⁺] |
|---|---|---|---|---|
| 14 | 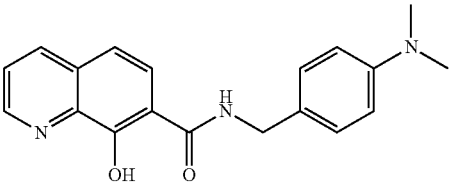<br>8-Hydroxy-N-(4-(dimethylamino)benzyl)quinoline-7-carboxamide | δ: 9.20 (t, 1H); 8.91 (dd, 1H); 8.34 (dd, 1H); 8.02 (d, 1H); 7.64 (dd, 1H); 7.41 (d, 1H); 7.21 (m, 2H); 6.71 (m, 2H); 4.46 (d, 2H); 2.86 (s, 6H). | A | 0.79; 322.1 |
| 15 | 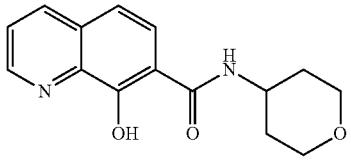<br>8-Hydroxy-N-(tetrahydro-2H-pyran-4-yl)quinoline-7-carboxamide | δ: 8.91 (dd, 1H); 8.70 (d, 1H); 8.35 (dd, 1H); 8.01 (d, 1H); 7.64 (dd, 1H); 7.42 (d, 1H); 4.01-4.28 (m, 1H); 3.78-4.01 (m, 2H); 3.44 (td, 2H); 1.76-2.01 (m, 2H); 1.53-1.72 (m, 2H). | A | 0.92; 273.1 |
| 16 | 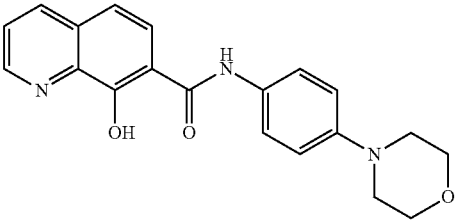<br>8-Hydroxy-N-(4-morpholinophenyl)quinoline-7-carboxamide | δ: 10.63 (br. s, 1H); 8.93 (dd, 1H); 8.43 (dd, 1H); 8.07 (d, 1H); 7.69 (dd, 1H); 7.52-7.65 (m, 2H); 7.44 (d, 1H); 6.86-7.11 (m, 2H); 3.61-3.89 (m, 4H); 2.95-3.27 (m, 4H). | A | 1.05; 350.2 |
| 17 | 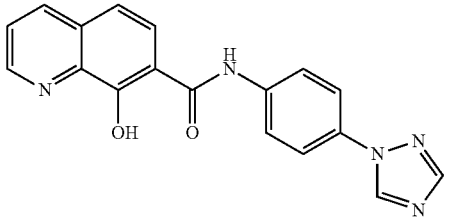<br>8-Hydroxy-N-(4-(1H-1,2,4-triazol-1-yl)phenyl)quinoline-7-carboxamide | δ: 11.28 (br. s, 1H); 9.25 (s, 1H); 8.94 (dd, 1H); 8.50 (dd, 1H); 8.22 (s, 1H); 8.05 (d, 1H); 7.90 (m, 4H); 7.74 (dd, 1H); 7.42 (d, 1H). | A | 1.16; 332.1 |
| 18 | 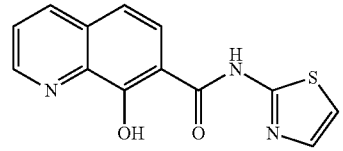<br>8-Hydroxy-N-(thiazol-2-yl)quinoline-7-carboxamide | (353K) δ: 8.90 (dd, 1H); 8.50 (dd, 1H); 8.13 (d, 1H); 7.74 (dd, 1H); 7.51 (d, 1H); 7.31 (d, 1H); 7.19 (d, 1H). | A | 1.11; 272.0 |
| 19 | 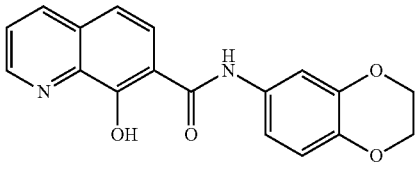<br>8-Hydroxy-N-(2,3-dihydrobenzo[b][1,4]dioxin-6-yl)quinoline-7-carboxamide | δ: 10.72 (br. s, 1H); 8.93 (dd, 1H); 8.45 (dd, 1H); 8.03 (d, 1H); 7.70 (dd, 1H); 7.43 (d, 1H); 7.40 (d, 1H); 7.11 (dd, 1H); 6.86 (d, 1H); 4.12-4.37 (m, 4H). | A | 1.43; 323.2 |

TABLE 2-continued

| Ex. | Chemical name | $^1$H-NMR (DMSO-$d_6$) | LC-MS method | $R_t$; [MH$^+$] |
|---|---|---|---|---|
| 20 | 8-Hydroxy-N-(4-morpholinobenzyl)quinoline-7-carboxamide | δ: 9.22 (t, 1H); 8.91 (dd, 1H); 8.35 (dd, 1H); 8.02 (d, 1H); 7.64 (dd, 1H); 7.42 (d, 1H); 7.25 (m, 2H); 6.92 (m, 2H); 4.49 (d, 2H); 3.60-3.90 (m, 4H); 2.93-3.18 (m, 4H). | A | 1.10; 364.1 |
| 21 | 8-Hydroxy-N-((5-methylisoxazol-3-yl)methyl)quinoline-7-carboxamide | δ: 9.38 (t, 1H); 8.92 (dd, 1H); 8.36 (dd, 1H); 7.99 (d, 1H); 7.66 (dd, 1H); 7.42 (d, 1H); 6.22 (s, 1H); 4.59 (d, 2H); 2.38 (s, 3H). | A | 1.10; 284.2 |
| 22 | 8-Hydroxy-N-((4-methylthiazol-2-yl)methyl)quinoline-7-carboxamide | δ: 9.59 (t, 1H), 8.93 (dd, 1H); 8.38 (dd, 1H), 8.01 (d, 1H), 7.67 (dd, 1H), 7.44 (d, 1H), 7.16 (q, 1H), 4.83 (d, 2H), 2.35 (s, 3H) | A | 1.08; 300.2 |
| 23 | 8-Hydroxy-N-(isoxazol-3-yl)methyl)quinoline-7-carboxamide | δ: 12.50 (br. s, 1H); 8.91 (dd, 1H); 8.85 (d, 1H); 8.61 (dd, 1H); 8.09 (d, 1H); 7.81 (dd, 1H); 7.30 (d, 1H); 7.13 (d, 1H). | A | 1.11; 256.1 |
| 24 | 8-Hydroxy-N-(benzo[d]thiazol-2-ylmethyl)quinoline-7-carboxamide | δ: 9.73 (t, 1H); 8.95 (dd, 1H); 8.39 (dd, 1H); 8.03-8.11 (m, 1H); 8.04 (d, 1H); 7.91-8.01 (m, 1H); 7.69 (dd, 1H); 7.35-7.58 (m, 3H); 5.02 (d, 2H). | A | 1.50; 336.1 |
| 25 | 8-Hydroxy-N-((5-methylpyrazin-2-yl)methyl)quinoline-7-carboxamide | δ: 9.46 (t, 1H); 8.93 (dd, 1H); 8.57 (d, 1H); 8.50 (d, 1H); 8.37 (dd, 1H); 8.02 (d, 1H); 7.66 (dd, 1H); 7.44 (d, 1H); 4.70 (d, 2H); 2.49 (br. s, 3H). | A | 0.98; 295.2 |
| 26 | 8-Hydroxy-N-((1-methyl-1H-imidazol-2-yl)methyl)quinoline-7-carboxamide | δ: 9.28 (t, 1H); 8.92 (dd, 1H); 8.36 (d, 1H); 8.05 (d, 1H); 7.66 (dd, 1H); 7.43 (d, 1H); 7.11 (d, 1H); 6.83 (d, 1H); 4.64 (d, 2H); 3.69 (s, 3H). | B | 2.39; 283.2 |

TABLE 2-continued

| Ex. | Chemical name | $^1$H-NMR (DMSO-$d_6$) | LC-MS method | $R_t$; [MH$^+$] |
|---|---|---|---|---|
| 27 | 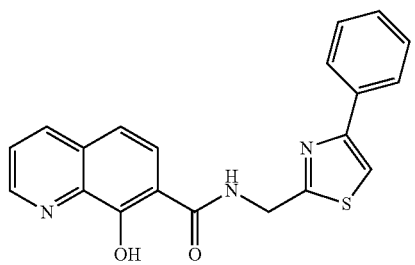<br>8-Hydroxy-N-((4-phenylthiazol-2-yl)methyl)quinoline-7-carboxamide | δ: 9.75 (t, 1H); 8.94 (dd, 1H); 8.38 (dd, 1H); 8.01-8.07 (m, 2H); 7.93-8.00 (m, 2H); 7.67 (dd, 1H); 7.40-7.52 (m, 3H); 7.27-7.39 (m, 1H); 4.94 (d, 2H). | A | 1.74; 362.1 |
| 28 | 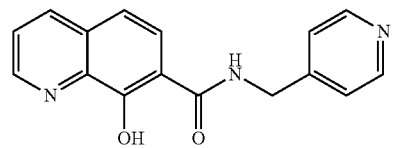<br>8-Hydroxy-N-(pyridin-4-ylmethyl)quinoline-7-carboxamide | δ: 9.40 (t, 1H); 8.93 (dd, 1H); 8.44-8.61 (m, 2H); 8.37 (dd, 1H); 8.02 (d, 1H); 7.66 (dd, 1H); 7.45 (d, 1H); 7.28-7.41 (m, 2H); 4.63 (d, 2H). | B | 2.04; 280.1 |
| 29 | 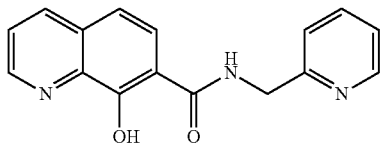<br>8-Hydroxy-N-(pyridin-2-ylmethyl)quinoline-7-carboxamide | δ: 9.46 (t, 1H); 8.93 (dd, 1H); 8.54 (ddd, 1H); 8.37 (dd, 1H); 8.06 (d, 1H); 7.78 (td, 1H); 7.66 (dd, 1H); 7.45 (d, 1H); 7.41 (d, 1H); 7.29 (ddd, 1H); 4.70 (d, 2H) | A | 0.57; 280.1 |

2. Activity Testing: Methods and Results

Organisms Used to Test Antifungal Activity

*Trichophyton Rubrum* (ATCC 28188, PBI International); *Trichophyton Mentagrophytes* (ATCC 9533, PBI International); *Aspergillus Niger* (ATCC 16404, PBI International); *Scopulariopsis Brevicaulis* (ATCC 36840, DSMZ); *Candida Albicans* (ATCC 90028, PBI International); *Candida Glabrata* (ATCC 90030, DSMZ).

Preparation and Conservation

Strains were prepared from freeze-dried ampoules or freeze-dried pellets. An isolation of the suspensions was made on Potato Dextrose Agar (PDA) to test the strains purity. A strains' massive growth was then made streaking microbial suspensions on PDA plates.

Incubation was at 30° C. for 48-72 Hours (*Candida* yeasts) and for 7-10 days (filamentous fungi).

The yeasts' colonies and the filamentous fungi's conidia were harvested with 3-5 mL of RPMI 1640+50% glycerol and the aliquots frozen at −80° C.

Antifungal Susceptibility Testing

Compounds' minimal inhibition concentration (MIC) was determined through broth micro-dilution susceptibility test using a method developed in agreement with the National Committee for Clinical Laboratory Standards (NCCLS) (National Committee for Clinical Laboratory Standards. Reference Method for Broth Dilution Antifungal Susceptibility Testing of Yeasts; Approved standard-Second Edition M27-A2. 2002; Vol. 22, No. 15) (National Committee for Clinical Laboratory Standards. Reference Method for Broth Dilution Antifungal Susceptibility Testing of Filamentous Fungi; Approved standard M38-A. 2002; Vol. 22, No. 16).

Assays were carried out in RPMI 1640 with L-glutamine medium buffered to pH 7 with 0.165M 3-(N-morpholino) propanesulfonic acid (MOPS) and 10M NaOH and supplemented with 18 g glucose/liter. The tests were performed using 96 well sterile plates (inoculum size of 1×10$^5$ CFU/mL). Compounds stock solutions were prepared at 12.8 mg/mL in 100% DMSO. A series of twofold dilutions were prepared in plate using RPMI 1640. Final concentrations ranged from 0.125 to 128 µg/mL at 1% DMSO.

MIC is defined as the lowest concentration of antifungal agent which prevents any visible growth and was determined after 48 h of incubation for yeasts (35° C.) and after five days of incubation for filamentous fungi (35° C.).

Results

The MIC values for the most preferable compounds, calculated as the geometric means of the values obtained in two single experiments, are reported in Table 3.

TABLE 3

| Ex | Trycophyton Rubrum ATCC 28188 | Tricophyton Mentagrophytes ATCC 9533 | Aspergillus Niger ATCC 16404 | Scopulariopsis Brevicaulis ATCC 36840 | Candida Albicans ATCC 90028 | Candida Glabrata ATCC 90030 |
|---|---|---|---|---|---|---|
| 1 | 0.50 | 0.50 | 0.25 | 0.25 | 1.00 | 1.00 |
| 2 | 1.00 | 0.71 | 0.35 | 2.00 | 1.41 | 1.41 |
| 3 | 0.35 | 0.18 | 0.18 | 0.35 | 1.00 | 1.00 |
| 4 | 0.71 | 0.50 | 0.35 | 0.71 | 2.00 | 1.00 |
| 5 | 0.35 | 0.50 | 0.71 | 0.71 | 0.50 | 0.71 |
| 6 | 1.41 | 1.00 | 0.50 | 1.41 | 1.41 | 1.41 |
| 7 | 0.50 | 0.71 | 0.50 | 2.00 | 0.50 | 1.00 |
| 8 | 0.71 | 0.50 | 0.25 | 1.00 | 2.00 | 2.00 |
| 9 | 0.71 | 1.00 | 1.00 | 0.71 | 0.71 | 0.71 |
| 10 | 2.00 | 2.00 | 1.00 | 1.00 | 4.00 | 11.31 |
| 11 | 1.00 | 1.00 | 1.00 | 1.00 | 2.00 | 1.41 |
| 12 | 1.41 | 1.00 | 0.71 | 1.41 | 1.41 | 1.41 |
| 14 | 1.00 | 0.71 | 0.50 | 1.00 | 2.83 | 1.41 |
| 17 | 2.52 | 2.00 | 1.00 | 1.26 | 2.00 | 2.83 |
| 19 | 0.25 | 0.50 | 1.00 | 1.00 | 2.00 | 2.00 |
| 20 | 1.00 | 0.50 | 0.50 | 4.00 | 4.00 | 2.00 |
| 21 | 1.00 | 4.00 | 1.00 | 2.83 | 2.00 | 2.00 |
| 22 | 1.41 | 2.83 | 1.00 | 1.00 | 2.00 | 2.00 |
| 24 | 2.00 | 1.00 | 0.50 | 1.00 | 2.00 | 2.83 |
| 29 | 2.00 | 2.00 | 0.50 | 1.00 | 4.00 | 4.00 |

Furthermore, the compound codified as E8 in EP1669348A1 was synthesized together with a new compound (codified as NiK-29298), not included among those disclosed in EP1669348A1, nor in the present invention, that can be used as a link between the class of compound described in the present application and those described in EP1669348A1 (Table 4).

TABLE 4

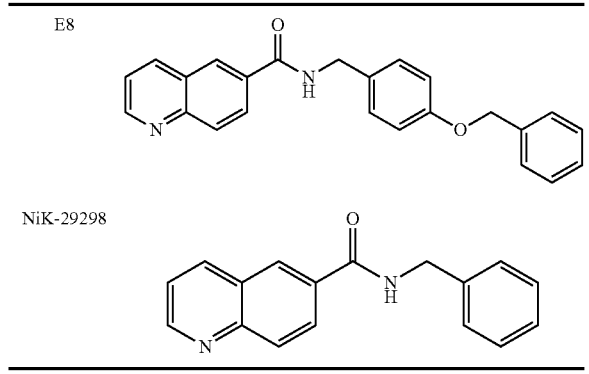

The MIC values for these compounds, tested on the same organisms used to assess the potency of the derivatives described in the present application are reported in Table 5.

TABLE 5

| Ex | Trycophyton Rubrum ATCC 28188 | Tricophyton Mentagrophytes ATCC 9533 | Aspergillus Niger ATCC 16404 | Scopulariopsis Brevicaulis ATCC 36840 | Candida Albicans ATCC 90028 | Candida Glabrata ATCC 90030 |
|---|---|---|---|---|---|---|
| E8 | >128 | 75 | 2-128 | >128 | 1.41 | 1.00 |
| NiK-29298 | >128 | 128 | 64-128 | >128 | 2.00 | 5.65 |

As it can be appreciated, all the compounds listed in table 3 are active on all the 6 strains tested, including yeasts, dermatophytes and molds. This broad spectrum of the compounds of the present invention accounts for a predicted efficacy on all kinds of fungal infections in humans or in animals, including skin, scalp and nail infections, mostly caused by dermatophytes; vaginal, mouth and intestinal infections, mostly caused by yeasts; ear, pulmonary, eye, and other systemic infections, mostly caused by molds.

Conversely, the compound E8, disclosed in EP1669348A1, and the compound NiK-29298, characterized by the same quinoline scaffold described in EP1669348A1, are active only on yeasts and do not display any appreciable activity against the other strains, including dermatophytes and molds.

Mechanism of Action

It is known in the art that ciclopirox, one of the most potent and broad spectrum antifungal agents, kills the fungal cells by chelating $Fe^{3+}$, i.e. by subtracting the iron ions from the fungal cells, and its in vitro action is inhibited only by adding an adequate quantity of $Fe^{3+}$ ions to the medium. Ciclopirox is also known in the art to be the only antifungal agent which, due to its peculiar mechanism of action, does not induce resistances in fungal strains.

Method for the Assessment of the Mechanism of Action

To verify if the compounds mechanism of action is the chelation of iron ions, the MIC determination with Candida glabrata (ATCC 90030) strain was performed by the addition of excessive iron ions (100 μM $FeCl_3$) in the test medium. The viability of cells exposed to drugs, with or without the metal ion $Fe^{3+}$, was evaluated by the OD measure at 540 nm.

The potency of compounds described in Example 3, 4, 11 12, E8 and NiK-29298 were evaluated on Candida glabrata in presence and in absence of 100 μM (100 micromoles) $Fe^{3+}$.

The results are reported in the following FIGS. 1, 2 and 3.

In all figures, the lines and dots represent the percent inhibition of the fungal growth (in ordinate) by adding different concentrations of antifungal agents (in abscissa). Blue lines and dots are the experiments performed without iron supplementation, while red lines and dots represent the results of the experiments performed in presence of 100 μM $Fe^{3+}$. As known from the art, ciclopirox effect is completely inhibited by presence of $Fe^{3+}$ and *Candida glabrata* is able to grow normally (FIG. 1). Conversely, $Fe^{3+}$ has no effect on amphotericin, an antifungal agent known in the art to have a mechanism of action different from that of ciclopirox.

Figure 2:
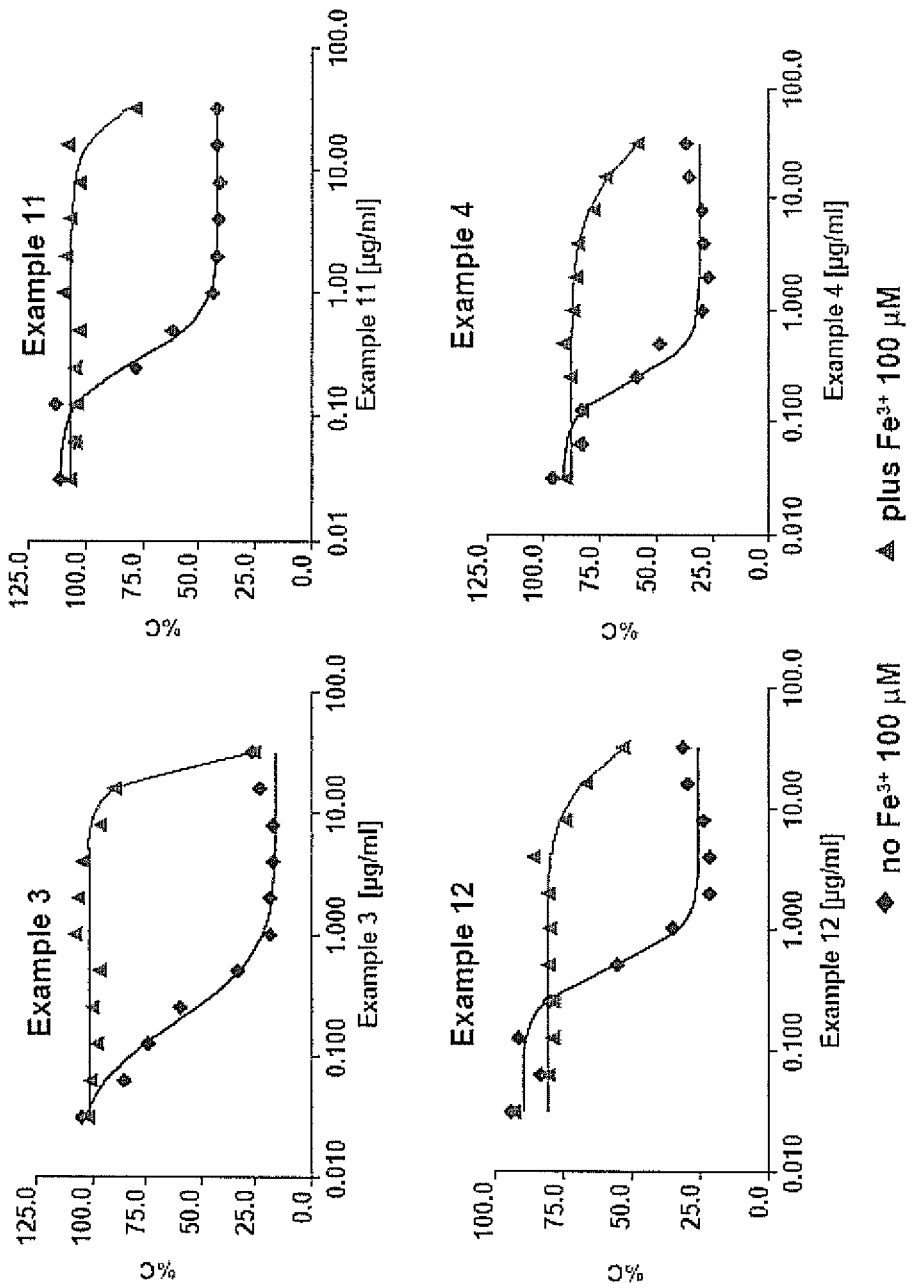
FIG. 2 shows the antifungal activity of the compounds of Examples 3, 4, 11, and 12 in the presence and absence of $Fe^{3+}$.
Figure 3:
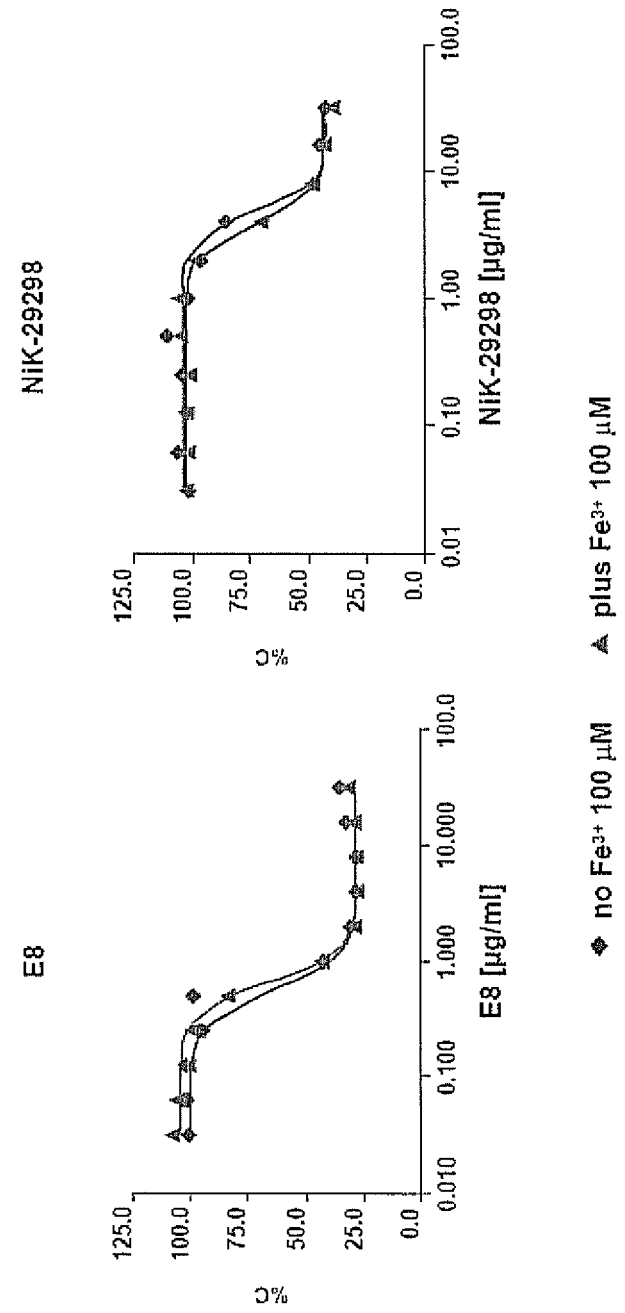
FIG. 3 shows the antifungal activity of E8 and NiK-29298 in the presence and absence of $Fe^{3+}$.

All the compounds of the present invention have similar behavior to ciclopirox, i.e. their antifungal activity is completely inhibited by presence of $Fe^{3+}$ (FIG. 2).

On the contrary, the compound E8, disclosed by EP1669348A1, and the compound NiK-29298, with the quinolone scaffold described in EP1669348A1, unlike ciclopirox and unlike the compounds of the present invention, where not inhibited by the presence of $Fe^{3+}$ ions in the medium culture.

In conclusion, the compounds disclosed in EP1669348A1 have a narrow spectrum of action, limited to yeasts, while they do not display antifungal activity against dermatophytes or molds. Moreover, their mechanism of action is independent on iron chelation.

On the contrary, the compounds of the present invention are superior to those disclosed in EP1669348A1, In that they have a potent antifungal activity with a wide spectrum of action, extended to yeasts, dermatophytes and molds. This characteristic makes their efficacy predictable in a variety of fungal infections, including skin, scalp, nail infections, moreover vaginal, mouth and intestinal infections, finally ear, pulmonary, eye, and other systemic infections. Furthermore, the compounds of the present invention are superior to those disclosed in EP1669348A1, in that their mechanism of action is iron chelation, a mechanism known in the art to avoid development of resistance in fungal cells.

The invention claimed is:
1. A method of treating a fungal infection, in a subject in need thereof, comprising administration of an effective amount of a compound of general formula (I)

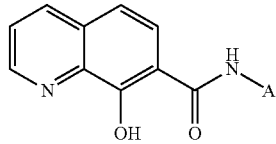

(I)

or a pharmaceutically acceptable salt or derivative thereof, wherein
A represents:
 —$(CH_2)_m$—$X_1$,
 —$(CH_2)_m$—$C_3$-$C_8$cycloalkyl,
 —$(CH_2)_m$—W—$X_2$,
 —$(CH_2)_m$—W—$CH_2$—$X_1$, or
 —$(CH_2)_m$—$CHR_9$—$(CH_2)_m$—$X_1$;
$X_1$ represents:
 -aryl, optionally substituted by one, two or three $R_4$,
 -heterocycle, optionally substituted by one or two $R_5$,
 —$C_1$-$C_8$alkyl,
 —CH(OH)-phenyl,
 —S-phenyl,
 —$NHSO_2$-phenyl,
 —CN,
 —OH,
 —$C_3$-$C_8$cycloalkyl, or
 -4-cyano-2,3,4,5-tetrafluoro-phenyl;
$X_2$ represents:
 -aryl,
 -heterocycle,
 —$C_1$-$C_8$alkyl,
 —CH(OH)-phenyl, or
 —$C_3$-$C_8$cycloalkyl;
W represents:
 —NH—,
 —O—, or
 —S—;
$R_4$ represents:
 —F,
 —Cl,
 —Br,
 —I,
 —$NO_2$,
 —$CF_3$,
 —CN,
 —$CH_2OH$
 —$C_1$-$C_6$alkyl,
 —W—$R_{10}$
 —$(CH_2)_m$-aryl,
 —$(CH_2)_m$-heterocycle,
 —$(CH_2)_m$—$C_3$-$C_8$cycloalkyl
 —$SO_2$—NH-heterocycle,
 —$(CH_2)_m$—$NR_{14}R_{15}$,
 —$(SO_2)$—$NR_{14}R_{15}$;
 —(C=O)—$NR_{14}R_{15}$, or
 —(N—C=O)—$NR_{14}R_{15}$;
$R_5$ represents:
 —H,
 —F,
 —Cl,
 —Br,
 —$CF_3$,
 —W—$R_{10}$,
 —$C_1$-$C_6$alkyl,
 —$(CH_2)_m$-aryl,
 —$(CH_2)_m$-heterocycle, or
 —$(CH_2)_m$—$C_3$-$C_8$cycloalkyl;
$R_9$ represents:
 —$C_1$-$C_7$alkyl,
 —$C_3$-$C_8$cycloalkyl,
 —$C(O)R_{11}$,
 —$C(O)NHR_{11}$,
 —$C(OH)R_{11}$,
 —$CH_2OH$,
 —$CO_2R_{11}$, or
 -aryl;
$R_{10}$ represents:
 —H,
 —$C_1$-$C_6$alkyl,
 —$(CH_2)_m$-aryl,
 —$(CH_2)_m$-heterocycle,
 —$(CH_2)_m$—$C_3$-$C_8$cycloalkyl, or
 —$CH(R_{12})R_{13}$;
$R_{11}$ represents:
 —H,
 —$C_1$-$C_7$alkyl,
 —$(CH_2)_mX_1$, or
 —$(CH_2)_m$—$C_3$-$C_8$cycloalkyl;
$R_{12}$ represents:
 —H,
 —$(CH_2)_mCO_2$—$C_1$-$C_6$alkyl,
 —$(CH_2)_m$-phenyl,
 —$(CH_2)_m$-heterocycle,
 —$C_1$-$C_6$alkyl,
 —$C_1$-$C_4$alkylNH—$COOCH_2$-benzyl, or
 —$C_1$-$C_4$alkyl-S—$CH_3$;

$R_{13}$ represents:
- —NH—$CO_2C(CH_3)_3$,
- —CN,
- —COOH, or
- —$CO_2R_{11}$;

$R_{14}$ and $R_{15}$, independently from each other, represent:
- —H,
- —$C_1$-$C_6$alkyl,
- —$(CH_2)_m$-aryl,
- —$(CH_2)_m$-cycloalkyl,
- —$(CH_2)_m$-heterocycle,
- —$(CH_2)_m$—W—$R_{10}$,
- —$(CH_2)_m$—CN,
- taken together with the nitrogen atom to which they are attached form an optionally substituted 5- to 8-membered heteromonocycle having from one to three additional heteroatoms selected from the group consisting of nitrogen, oxygen and sulphur, or
- taken together with the nitrogen atom to which they are attached form an optionally substituted 5- to 8-membered heteromonocycle which is fused to one or two optionally substituted saturated or unsaturated rings or to other optionally substituted heterocycles having from one to three heteroatoms selected from the group consisting of nitrogen, oxygen and sulphur; and m represents an integer from 0 to 6;

wherein aryl is:
- phenyl,
- naphthyl,
- biphenyl,
- tetrahydro-naphthyl, or
- fluorenyl;

heterocycle is a 5-, 6- or 7-membered saturated or unsaturated ring containing from one to three heteroatoms selected from the group consisting of nitrogen, oxygen and sulphur, and including any bicyclic group in which any of the above heterocyclic rings is fused to a benzene ring or another heterocyclic; and cycloalkyl is a saturated or unsaturated hydrocarbon ring including bicyclic groups in which the above ring is connected to a benzene, heterocyclic or other hydrocarbon ring.

2. The method according to claim 1, wherein A represents —$(CH_2)_m$—$X_1$.

3. The method according to claim 1, wherein m represents an integer from 0 to 1.

4. The method according to claim 1, wherein $X_1$ represents
- -aryl, optionally substituted by one or two $R_4$,
- -heterocycle, optionally substituted by one or two $R_5$, or
- —$C_3$-$C_8$cycloalkyl.

5. The method according to claim 1, wherein $R_4$ represents
- —Cl,
- —Br,
- —$CF_3$,
- —W—$R_{10}$, or
- —$(CH_2)_m$—$NR_{14}R_{15}$.

6. The method according to claim 1, wherein W represents oxygen.

7. The method according to claim 1, wherein $R_{10}$ represents
- —H, or
- —$C_1$-$C_6$alkyl.

8. The method according to claim 1, wherein $R_{14}$ and $R_{15}$, independently from each other, represent
- —$C_1$-$C_6$alkyl, or
- taken together with the nitrogen atom to which they are attached form an optionally substituted 5- to 8-membered heteromonocycle having from one to three additional heteroatoms selected from the group consisting of nitrogen, oxygen and sulphur.

9. The method according to claim 1, wherein aryl is phenyl.

10. The method according to claim 1,
wherein A represents —$(CH_2)_m$—$X_1$,
$X_1$ represents:
- -aryl, optionally substituted by one, two or three $R_4$,
- -heterocycle, optionally substituted by one or two $R_5$, or
- —$C_3$-$C_8$cycloalkyl, $R_4$ represents
- —Cl,
- —Br,
- —$CF_3$,
- —W—$R_{10}$, or
- —$(CH_2)_m$—$NR_{14}R_{15}$, $R_5$ represents —$C_1$-$C_6$ alkyl, $R_{10}$ represents
- —H, or
- —$C_1$-$C_6$alkyl, $R_{14}$ and $R_{15}$ represent —$C_1$-$C_6$alkyl, W represents oxygen, and m represents an integer from 0 to 1.

11. The method according to claim 1, wherein heterocycle is 2,3-dihydrobenzo[b][1,4]dioxine, pyridine, thiophene, triazole, thiazole, isoxazole, benzothiazole, pyrazine, imidazole or furan.

12. The method according to claim 1, wherein the compound of general formula (I) is selected from the group consisting of:
- 8-Hydroxy-N-(thiophen-2-ylmethyl)quinoline-7-carboxamide;
- 8-Hydroxy-N-(cyclohexylmethyl)quinoline-7-carboxamide;
- 8-Hydroxy-N-benzyl-quinoline-7-carboxamide;
- 8-Hydroxy-N-(4-chlorobenzyl)quinoline-7-carboxamide;
- 8-Hydroxy-N-(4-methoxyphenyl)quinoline-7-carboxamide;
- 8-Hydroxy-N-(4-(trifluoromethyl)benzyl)quinoline-7-carboxamide;
- 8-Hydroxy-N-phenyl-quinoline-7-carboxamide;
- 8-Hydroxy-N-(2-hydroxybenzyl)quinoline-7-carboxamide;
- 8-Hydroxy-N-(furan-2-ylmethyl)quinoline-7-carboxamide;
- 8-Hydroxy-N-(pyridin-3-ylmethyl)quinoline-7-carboxamide;
- 8-Hydroxy-N-(4-methoxybenzyl)quinoline-7-carboxamide;
- 8-Hydroxy-N-(4-bromobenzyl)quinoline-7-carboxamide;
- 8-Hydroxy-N-(1,1-dioxidotetrahydrothien-3-yl)quinoline-7-carboxamide;
- 8-Hydroxy-N-(4-(dimethylamino)benzyl)quinoline-7-carboxamide;
- 8-Hydroxy-N-(tetrahydro-2H-pyran-4-yl)quinoline-7-carboxamide;
- 8-Hydroxy-N-(4-morpholinophenyl)quinoline-7-carboxamide;
- 8-Hydroxy-N-(4-(1H-1,2,4-triazol-1-yl)phenyl)quinoline-7-carboxamide;
- 8-Hydroxy-N-(thiazol-2-yl)quinoline-7-carboxamide;

8-Hydroxy-N-(2,3-dihydrobenzo[b][1,4]dioxin-6-yl)quinoline-7-carboxamide;
8-Hydroxy-N-(4-morpholinobenzyl)quinoline-7-carboxamide;
8-Hydroxy-N-((5-methylisoxazol-3-yl)methyl)quinoline-7-carboxamide;
8-Hydroxy-N-((4-methylthiazol-2-yl)methyl)quinoline-7-carboxamide;
8-Hydroxy-N-(isoxazol-3-yl)quinoline-7-carboxamide;
8-Hydroxy-N-(benzo[d]thiazol-2-ylmethyl)quinoline-7-carboxamide;
8-Hydroxy-N-((5-methylpyrazin-2-yl)methyl)quinoline-7-carboxamide;
8-Hydroxy-N-((1-methyl-1H-imidazol-2-yl)methyl)quinoline-7-carboxamide;
8-Hydroxy-N-((4-phenylthiazol-2-yl)methyl)quinoline-7-carboxamide;
8-Hydroxy-N-(pyridin-4-ylmethyl)quinoline-7-carboxamide; and
8-Hydroxy-N-(pyridin-2-ylmethyl)quinoline-7-carboxamide.

13. The method according to claim 1, wherein the fungal infection is from *Tricophyton Rubrum, Tricophyton Mentagrophytes, Aspergillus Niger, Scopulariopsis Brevicaulis* or *Candida*.

14. The method according to claim 13, wherein the fungal infection is from *Candida Albicans* or *Candida Glabrata*.

15. The method according to claim 1, wherein the fungal infection is from dermatophytes and/or molds.

16. The method according to claim 1, wherein the fungal infection is from *Tricophyton Rubrum, Tricophyton Mentagrophytes, Aspergillus Niger* and/or *Scopulariopsis Brevicaulis*.

17. The method according to claim 1, wherein the fungal infection is not from yeasts.

18. The method according to claim 1, wherein the fungal infection is not from *Candida*.

19. The method according to claim 1, wherein the subject is a mammal.

20. The method according to claim 19, wherein the subject is a human.

* * * * *

UNITED STATES PATENT AND TRADEMARK OFFICE
CERTIFICATE OF CORRECTION

PATENT NO. : 8,969,380 B2
APPLICATION NO. : 13/519439
DATED : March 3, 2015
INVENTOR(S) : Stefania Gagliardi et al.

It is certified that error appears in the above-identified patent and that said Letters Patent is hereby corrected as shown below:

Title Page, Item (56) Foreign Patent Documents: "EP1 6694348 6/2008" should be
--EP 16694348 6/2006--.

Title Page, Item (56) Other Publications: "Dictar M. O. et al, Med Mycol., 2000; 38 Suppl. 1, 251-256" should be
--Dictar M. O. et al, Med Mycol., 2000; 38 Suppl. 1, 251-258--.

Title Page, Item (56) Other Publications: "Trot R.J. et al" should be --Trof R.J. et al--.

Signed and Sealed this
Sixth Day of October, 2015

Michelle K. Lee
*Director of the United States Patent and Trademark Office*